United States Patent [19]

Barreras, Sr. et al.

[11] Patent Number: 5,895,416

[45] Date of Patent: Apr. 20, 1999

[54] METHOD AND APPARATUS FOR CONTROLLING AND STEERING AN ELECTRIC FIELD

[75] Inventors: Francisco J. Barreras, Sr., Miami; Oscar Jimenez, Coral Gables, both of Fla.

[73] Assignee: Medtronic, Inc., Minneapolis, Minn.

[21] Appl. No.: 08/814,917

[22] Filed: Mar. 12, 1997

[51] Int. Cl.[6] .................................................. A61N 1/08
[52] U.S. Cl. ........................... 607/62; 607/46; 607/2; 607/117; 607/148; 600/585; 600/547; 606/129
[58] Field of Search ............................ 600/585, 434, 600/547, 395; 606/129; 607/116–118, 122, 46, 66, 67, 45, 2, 148

[56] References Cited

U.S. PATENT DOCUMENTS

| 4,285,347 | 8/1981 | Hess ........................... 600/585 |
| 4,799,496 | 1/1989 | Hargreaves et al. ........... 600/585 |
| 5,336,182 | 8/1994 | Lundquist et al. ............. 600/585 |
| 5,345,937 | 9/1994 | Middleman et al. ........... 600/434 |
| 5,392,791 | 2/1995 | Nyman ......................... 600/585 |
| 5,417,719 | 5/1995 | Hull et al. . |
| 5,480,421 | 1/1996 | Otten ........................... 607/122 |
| 5,501,703 | 3/1996 | Holscheimer et al. . |
| 5,636,634 | 6/1997 | Kordis et al. ................. 600/585 |
| 5,643,330 | 7/1997 | Holsheimer et al. .......... 607/117 |

FOREIGN PATENT DOCUMENTS 9320887   10/1993   WIPO .
8600234   1/1996    WIPO .

OTHER PUBLICATIONS

IEEE Transactions On Biomedical Engineering, vol. 26, No. 8, Aug. 1989, "Orderly Stimulation Of Skeletal Muscle Motor Units With Tripolar Nerve Cuff Electrode", Baratta et al., pp. 836–843.

*Primary Examiner*—William E. Kamm
*Assistant Examiner*—Kennedy J. Schaetzle
*Attorney, Agent, or Firm*—Thomas R. Vigil

[57] ABSTRACT

The electric field steering assembly is used to control the size and/or location of, and/or steer the position of, an electric field in a living creature. The assembly comprises a pulse generator or stimulator, at least one implanted lead coupled to the stimulator and having, at a distal end thereof, at least three spaced apart electrodes, and electrical circuitry for adjusting the current and/or voltage at each electrode. The electrical circuitry is programmed to: 1) electronically change the size and/or location of an electric field established between the electrodes by independently programming the current flowing through of one or more anode (+) electrode(s) from one or more cathode (−) electrode(s), thereby steering the size and location of the electric field to recruit only target certain tissue and exclude unwanted tissue; and, 2) automatically change the voltage amplitude at each anode in response to changes in electrode impedance in order to maintain a constant anodic current, thereby preserving, for the duration of the therapy, the original electric field found to be effective at implant time.

25 Claims, 9 Drawing Sheets

TABLE A

| ELECTRIC FIELD | LEFT ELECTRODE | CENTER ELECTRODE | RIGHT ELECTRODE |
|---|---|---|---|
| A | +0.5 mA | 0 VOLT | +0.5 mA |
| B | +1.0 mA | 0 VOLT | +1.0 mA |
| C | +1.5 mA | 0 VOLT | +1.5 mA |
| D | +2.0 mA | 0 VOLT | +2.0 mA |
| E | +2.5 mA | 0 VOLT | +2.5 mA |
| F | +3.0 mA | 0 VOLT | +3.0 mA |

TABLE B

| ELECTRIC FIELD | LEFT ELECTRODE | CENTER ELECTRODE | RIGHT ELECTRODE |
|---|---|---|---|
| G | 0 VOLT | +1.0 mA | +0.5 mA |
| H | 0 VOLT | +2.0 mA | +1.0 mA |
| I | 0 VOLT | +3.0 mA | +1.5 mA |
| J | 0 VOLT | +4.0 mA | +2.0 mA |
| K | 0 VOLT | +5.0 mA | +2.5 mA |
| L | 0 VOLT | +6.0 mA | +3.0 mA |
| M | +0.5 mA | +1.0 mA | 0 VOLT |
| N | +1.0 mA | +2.0 mA | 0 VOLT |
| O | +1.5 mA | +3.0 mA | 0 VOLT |
| P | +2.0 mA | +4.0 mA | 0 VOLT |
| Q | +2.5 mA | +5.0 mA | 0 VOLT |
| R | +3.0 mA | +6.0 mA | 0 VOLT |

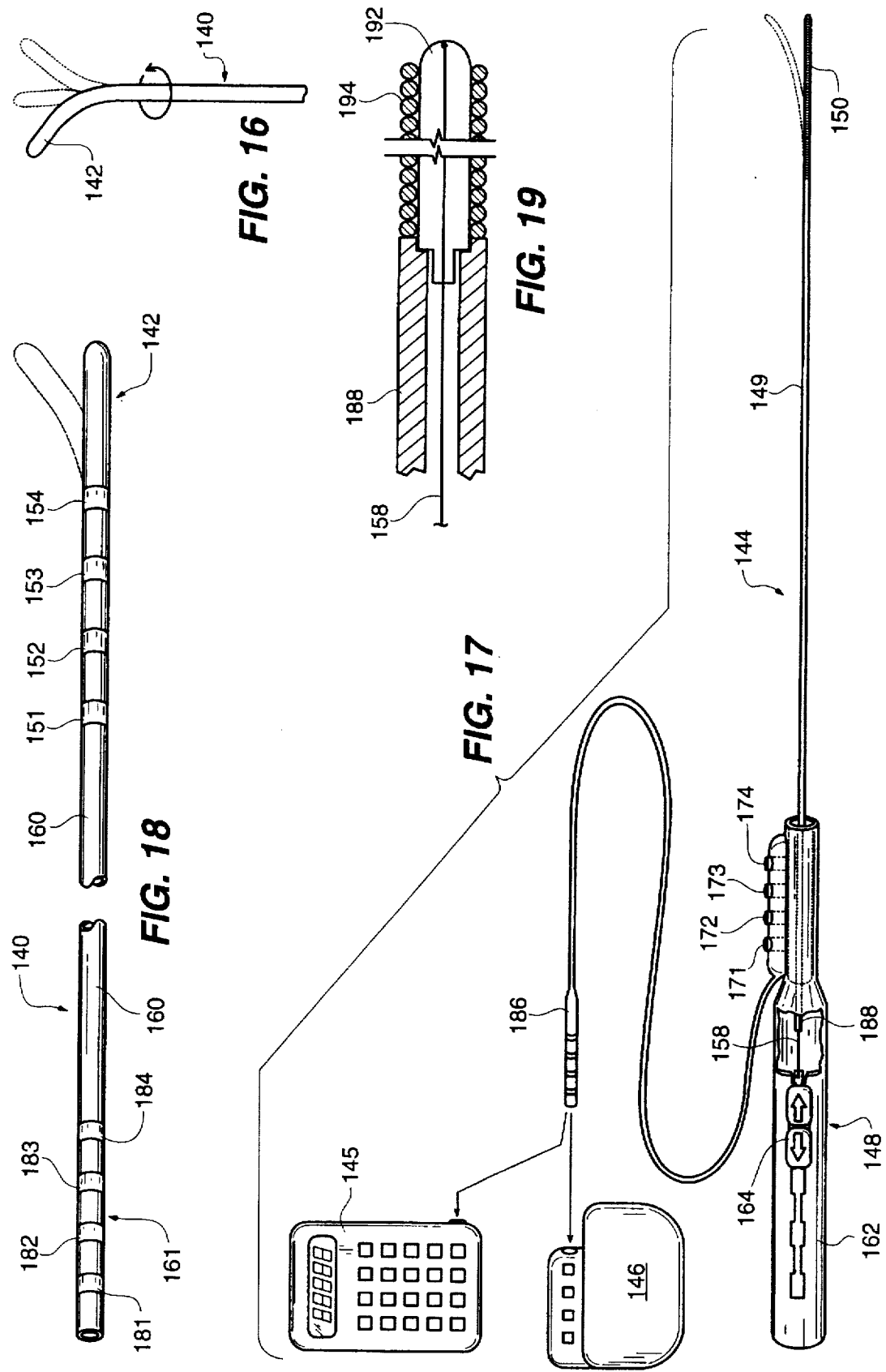

METHOD AND APPARATUS FOR CONTROLLING AND STEERING AN ELECTRIC FIELD

BACKGROUND OF THE INVENTION

1. Field of the Invention

The present invention relates to a method and apparatus for electrically and selectively stimulating specific nerve tissue in a living creature, namely a human being, by controlling and steering an electric field. More specifically, the present invention is directed to:

1) a spinal cord stimulator capable of electronically changing the size and/or location of the electric field by independently adjusting the current flowing through two or more anode (+) electrodes from one or more constant voltage cathode (−) electrode(s);

2) circuitry for automatically changing the voltage amplitude at each anode in response to changes in the electrode impedance in order to maintain a constant anodic current, thereby preserving for the duration of the therapy the original electric field found to be most effective at implant time;

3) a percutaneous stimulating lead incorporating a mechanical steering system capable of steering the lead's distal end around anatomical obstacles within the epidural space.

2. Description of the related art including information disclosed under 37 CFR §§ 1.97–1.99

The concept of using electrical stimulation for treating specific diseases or physical disorders is well known. Examples of electrical stimulators are: Cardiac pacemakers which restore a sick human heart to a normal rhythm, and neurological stimulators which control nerve or brain response (such as pain or epileptic seizures).

The use of a surgically implantable, electrical neurological stimulator has been well established for a number of years, especially for the control of nerve or brain response to treat intractable pain, epileptic seizures and tremors as a result of Parkinson disease. An example of a prior art device is an implantable neural stimulator powered by radio frequency (RF) or a non-rechargeable battery. Either neural stimulator incorporates the capability to designate: 1) which electrode(s) are to be used to deliver a negative stimulus pulse and which electrode(s) are to serve as the ground (return) path; 2) the pulse width of the negative stimulus pulses; 3) the voltage amplitude of the negative stimulus pulses; and, 4) the repetition rate of said stimulation pulses modulation.

A deficiency with this prior art device is that the resulting electric field (nerve recruiting area) is relatively broad and unfocused, sometimes resulting in undesirable motor responses. For the purpose of stimulating the dorsal column the stimulating electrodes are typically placed in the posterior epidural space, and the stimulus current must pass through the dura. If the electrodes have to be placed sufficiently lateral to the midline so that it is near the intercostal nerve root in order to cover the pain area, the patient will experience unwanted motor responses such as painful chest wall or abdominal wall stimulation.

Another deficiency with this prior art device is that the spinal cord movement with body position changes affect the distance between the stimulating electrodes and the spinal cord, resulting in undesirable variations in the size and/or location of the electric field, altering the paresthesia pattern. Movement of the electrodes from the optimal position can be a major problem when the patient becomes active.

With the prior art devices, where only changes of electrodes are possible and the same stimulus pulses are applied to all selected electrodes, it is often difficult to direct the stimulation field to recruit only the target nerve tissue and exclude unwanted nerve tissue.

Yet another deficiency with this prior art device is its inability to compensate for changes in electrode impedance due to; 1) growth of connective tissue around the electrodes, 2) histological changes, and, 3) changes in lead position which alters the distance between the electrodes and the dura. When a constant voltage is applied across two electrodes, the resulting electron current produces a flow of ions through the adjacent nerve tissue. A precise rate of ion flow is required for the pain relief. However, the magnitude of this electron current (and rate of ion flow) is controlled by the impedance between the electrodes. When this impedance changes, the size and/or location of the electric field also changes.

Still another deficiency with this prior art device is related to the design of the stimulation lead which makes t difficult to maneuver the lead's distal end (containing the stimulating electrodes) around anatomical obstacles normally found within the epidural space, and to force the electrodes against the dura to reduce the energy required for stimulation. During lead placement, it is not uncommon for the physician to attempt multiple passes to overcome anatomical obstacles, such as fatty tissue. Then, after the lead's distal end finally reaches the desired vertebral bodies, the physician needs to again manipulate the lead to force the electrodes against the dura to achieve paresthesia with the lowest possible stimulus energy in order to prevent unwanted motor responses.

SUMMARY OF THE INVENTION

It is an objective of the present invention to provide a partially or completely implanted neurological stimulator, connected to at least one stimulating lead incorporating at its distal end three or more electrodes, the stimulator being capable of: 1) electronically changing the size and/or location of the electric field by independently programming the current flowing through of one or more anode (+) electrode (s) from one or more cathode (−) electrode(s), thereby steering the size and location of the electric field to recruit only the target nerve tissue and exclude unwanted nerve tissue; and, 2) automatically changing the voltage amplitude at each anode in response to changes in electrode impedance in order to maintain a constant anodic current, thereby preserving, for the duration of the therapy, the original electric field found to be effective at implant time.

Another aspect of the present invention is to provide a partially or completely implanted neurological stimulator, connected to two stimulating leads, each lead being placed at either side of the midline of the spinal cord, each lead incorporating at its distal end two or more electrodes, and the stimulator being capable of: 1) electronically changing the size and/or location of the electric field by independently programming the current flowing through of one or more anode (+) electrode(s) from one or more cathode (−) electrode(s), thereby steering the size and location of the electric field to recruit only the target nerve tissue and exclude unwanted nerve tissue; and, 2) automatically changing the voltage amplitude at each anode in response to changes in electrode impedance in order to maintain a constant anodic current, thereby preserving for the duration of the therapy the original electric field found to be effective at implant time.

Another aspect of the present invention is to provide a partially or completely implanted neurological stimulator, connected to three stimulating leads, one lead being placed at the midline with the other two leads being placed at either side of the midline, each lead incorporating at its distal end two or more electrodes, and the stimulator being capable of: 1) electronically changing the size and/or location of the electric field by independently programming the current flowing through of one or more anode (+) electrode(s) from one or more cathode (−) electrode(s), thereby steering the size and location of the electric field to recruit only the target nerve tissue and exclude unwanted nerve tissue; and, 2) automatically changing the voltage amplitude at each anode in response to changes in electrode impedance in order to maintain a constant anodic current, thereby preserving, for the duration of the therapy, the original electric field found to be effective at implant time.

Another aspect of the present invention is to provide a mechanical steering system for each of the leads, for the purpose of: 1) aiding the physician in guiding the lead through the epidural space up to the target vertebral body by steering the lead's distal end away from anatomical obstacles; and, 2) positioning the lead's distal end in close proximity to the dura for the purpose of obtaining paresthesia with the lowest possible electrical energy, thereby recruiting only the target nerve tissue and excluding unwanted nerve tissue.

BRIEF DESCRIPTION OF THE DRAWINGS

FIG. 16 is a fragmentary view of the distal tip of a stimulating lead which can be bent and then rotated for effecting a desired placement of the electrodes on the distal tip.

FIG. 17 is a block diagram of a neural stimulator system and lead steering mechanism on which a stimulating lead is mounted.

FIG. 18 is a longitudinal perspective view of the stimulating lead which is mounted on the steering mechanism shown in FIG. 17.

FIG. 19 is an enlarged longitudinal sectional view of the tip of the steering mechanism shown in FIG. 17.

DESCRIPTION OF THE PREFERRED EMBODIMENT(S)

Figure 1:
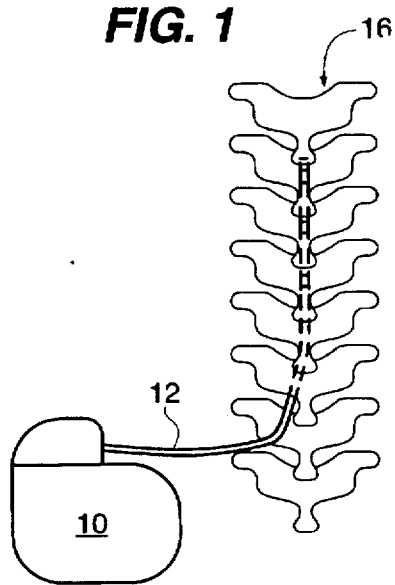
FIG. 1 is a block diagram of a single lead neural stimulator system constructed and operated according to the teachings of the present invention for steering an electric field.

In FIG. 1, there is illustrated a block diagram of a neurological electrical stimulator 10 and steerable lead 12 constructed according to the teachings of the present invention. The stimulator or pulse generator 10 and one or more steerable leads 12 form an electric field steering assembly constructed and operated according to the teachings of the present invention.

The stimulator 10 is connected to the single tripolar lead 12 percutaneously placed within the epidural space proximal to the target vertebrate bodies 16 and is capable of electrically modulating the size and location of the stimulating field 18 (FIG. 3) for the purpose of recruiting only the target nerve tissue and exclude unwanted nerve tissue.

Figure 2:
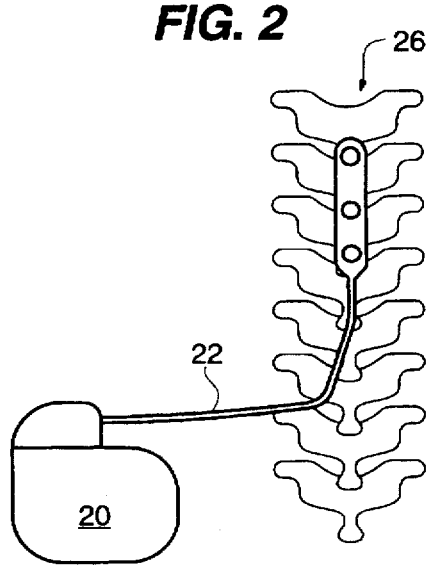
FIG. 2 is a block diagram of another single lead neural stimulator system constructed and operated according to the teachings of the present invention for steering an electric field.

In FIG. 2, there is illustrated a block diagram for a neurological electrical stimulator 20 and steerable lead 22, also constructed according to the teachings of the present invention. The stimulator 20 is connected to the single tripolar lead 22 placed proximal to the target vertebrate bodies 26 through a thoracic laminectomy and is capable of electrically modulating the size and location of the stimulating field 18 (FIG. 3) for the purpose of recruiting only the target nerve tissue and exclude unwanted nerve tissue.

Figure 3:
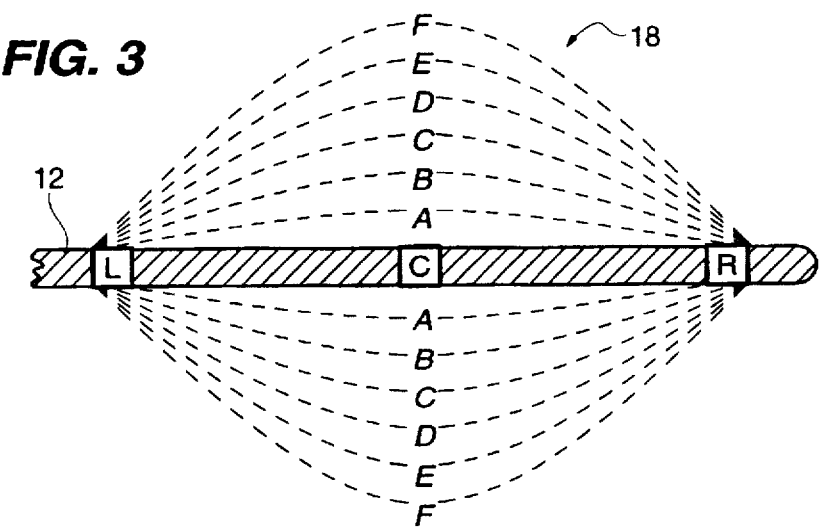
FIG. 3 is a longitudinal sectional view through a distal tip of a lead and shows electric fields established therewith by the voltage and currents set forth in TABLE A.

FIG. 3 illustrates the use of the single tripolar lead 12 or 22 and shows how the electric field 18 can be focused near a center electrode C by making the center electrode C negative and the left and right electrodes L and R positive and shows how the size of the electric field 18 can be changed by modulating the anodic currents listed in TABLE A at the positive electrodes L and R.

Figure 4:
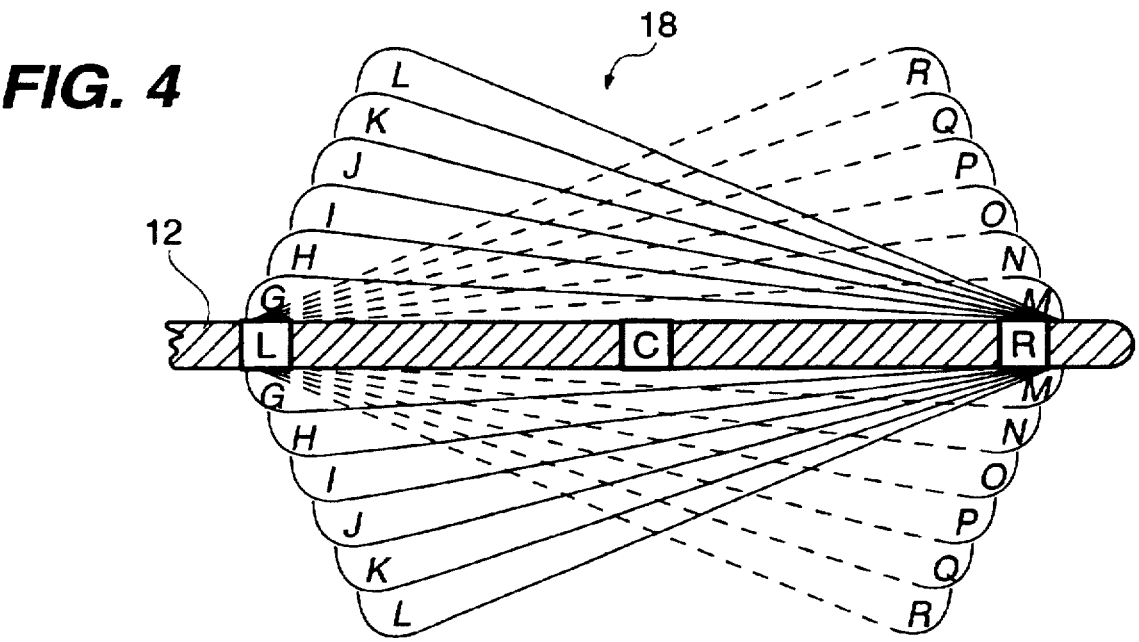
FIG. 4 is a longitudinal sectional view through a distal tip of a lead and shows electric fields established therewith by the voltage and currents set forth in TABLE B.

FIG. 4 illustrates how a single tripolar lead 12 or 22 can be used to focus the electric field 18 near the left electrode L by programming it to a higher current than the other two electrodes C and R and how the single tripolar electrode 12 or 22 can be used to focus the electric field 18 near the right electrode R by programming it to a higher current than the other two electrodes C and L and, further how the lead 12 or 22 can be used to control the size of the electric field by modulating the anodic current of the two higher current electrodes L and R with the currents listed in TABLE B.

Figure 5:
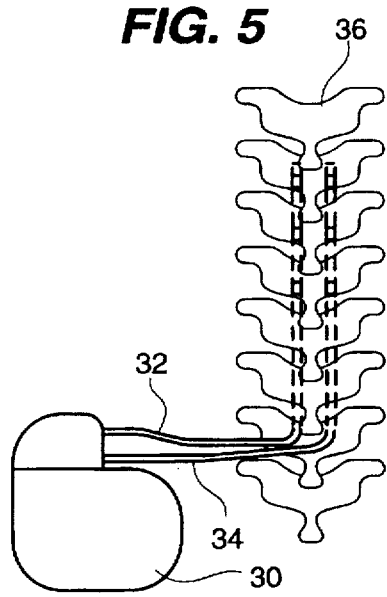
FIG. 5 is a block diagram of a two lead neural stimulator system constructed and operated according to the teachings of the present invention for steering an electric field.

FIG. 5 illustrates the use of a dual channel stimulator 30 with anodic current control connected to two percutaneous-epidural leads 32 and 34. Each lead 32, 34 is placed within the epidural space at either side of the midline proximal to the target vertebrate bodies 36. Each electrode 41–43 or 44–46 (FIG. 8) in each Lead 32 or 34 can be programmed positive (anode) or negative (cathode), and the anodic current at each positive electrode 41, 43 or 44, 46 can be programmed to a value different from the other anodes. Depending on the anodic current assigned to each electrode 41–46 and which electrode(s), e.g. 42 and 45, serve as the cathode, the size and location of the stimulating field, A, B or C, can be modulated for the purpose of recruiting only the target nerve tissue and exclude unwanted nerve tissue.

Figure 6:
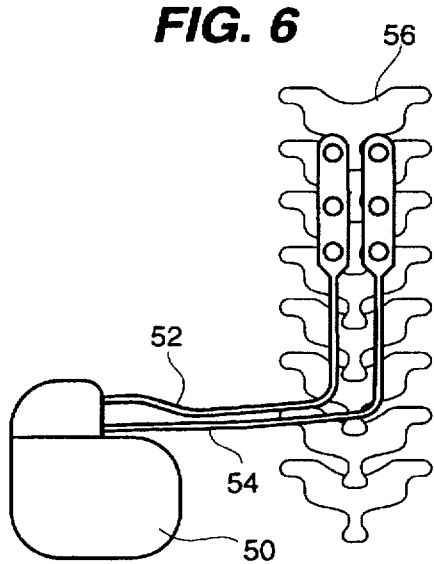
FIG. 6 is a block diagram of another two lead neural stimulator system constructed and operated according to the teachings of the present invention for steering an electric field.

FIG. 6 illustrates the use of a dual channel stimulator 50, with anodic current control, connected to two laminectomy leads 52, 54. Each lead 52, 54 is placed at either side of the midline proximal to the target vertebrate bodies 56. Each electrode 41–46 in each lead can be programmed positive (anode) or negative (cathode), and the anodic current of each positive electrode can be programmed to a value different from other anodes. Depending on the anodic current assigned to each electrode and which electrode(s) serve as the cathode, the size and location of the stimulating field, A, B or C, can be modulated for the purpose of recruiting only the target nerve tissue and exclude unwanted nerve tissue.

Figure 7:
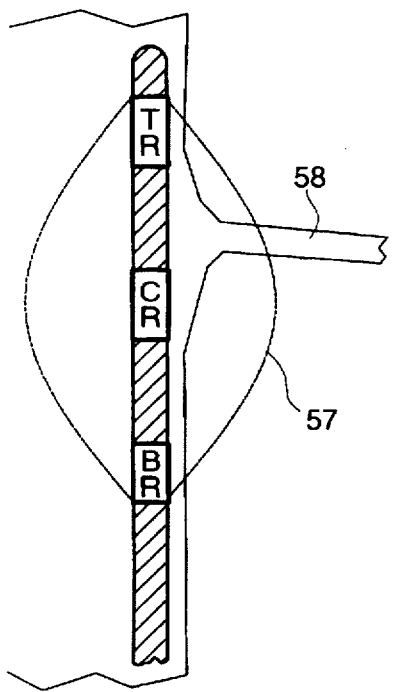
FIG. 7 is a longitudinal sectional view through a distal tip of a prior art lead and shows a typical prior art electric field established with the lead.

FIG. 7 illustrates a symmetrical electric field 57 generated by a prior art stimulator. In this case, although the intention is to recruit nerve tissue within the spinal cord corresponding to a pain area in the right side, the resulting electric field propagates uniformly around both sides of the electrodes also encircling a nerve root 58 nearby. Stimulation of the nerve root 58 results in unwanted motor responses, such as painful abdominal or chest wall stimulation.

Figure 8:
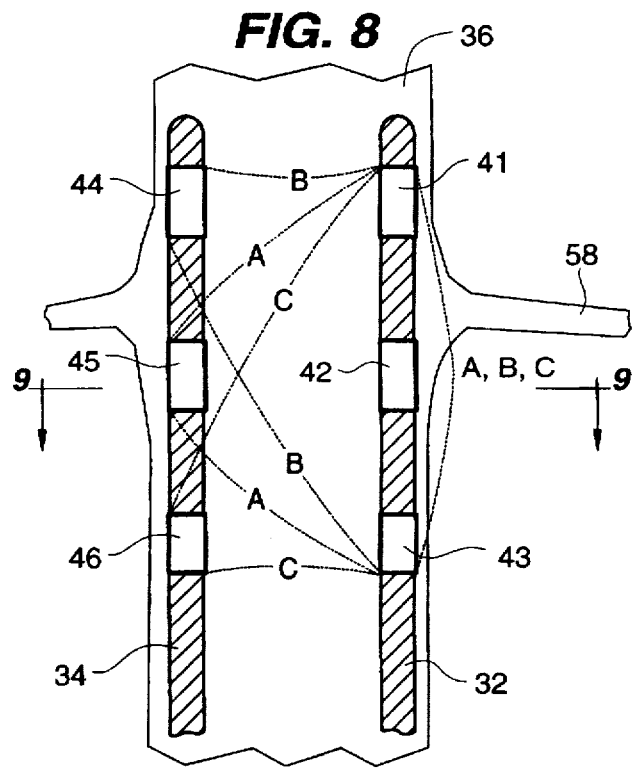
FIG. 8 is a longitudinal sectional view through the two distal tips of the two leads shown in FIG. 5 and shows three electric field configurations established therewith.

FIG. 8 illustrates how the size and location of the electric field can be modified in the present invention to achieve a paresthesia pattern covering the pain area without stimulating the nerve root. Two leads 32, 34 are placed at either side of the midline proximal to the target vertebrate bodies 36. Each electrode 41–43 or 44–46 in each lead 32,34 can be programmed positive (anode) or negative (cathode), and the anodic current of each positive electrode can be programmed to a value different from other anodes. Depending on the anodic current assigned to each electrode and which electrode(s) serve as the cathode, the size and location of the stimulating field can be controlled for the purpose of recruiting only the target nerve tissue and exclude unwanted nerve tissue. In this example, only three electric fields, A, B or C, are shown but it is obvious that many more are possible.

Electric field A is obtained by programming electrode 42 as the cathode, electrodes 41 and 43 as anodes programmed to equal current, and electrode 45 as an anode but programmed to a current higher than the current supplied to electrodes 41 and 43. The resulting electric field A is asymmetrical with a larger area at the left side of electrode 42 than at the right side, thereby missing the nerve root 58.

Electric field B is obtained by programming electrode 42 as the cathode, electrodes 41, 43 and 44 as the anodes but with the electrode 44 programmed, to a higher current than at the electrodes 41 and 43. The resulting electric field B is asymmetrical with a larger area at the top-left side of electrode 42 than at the right-center side, thereby missing the nerve root 58.

Electric field C is obtained by programming electrode 42 as the cathode, electrodes 41, 43 and 46 as the anodes but with the electrode 46 programmed to a current higher than at electrodes 41 and 43. The resulting electric field C is asymmetrical with a larger area at the bottom-left side of the electrode 42 than at the right-center side, thereby missing the nerve root 58.

Figure 9:
FIG. 9 is a sectional view through spaced apart electrodes shown in FIG. 8 and is taken along line 9—9 of FIG. 8.

FIG. 9 is a cross-sectional view of the electric field that forms between the electrode 42 and the electrodes 44/45/46, illustrating the pulling effect of the higher-current anodes 44/45/46 (away from the nerve root 58).

Figure 10:
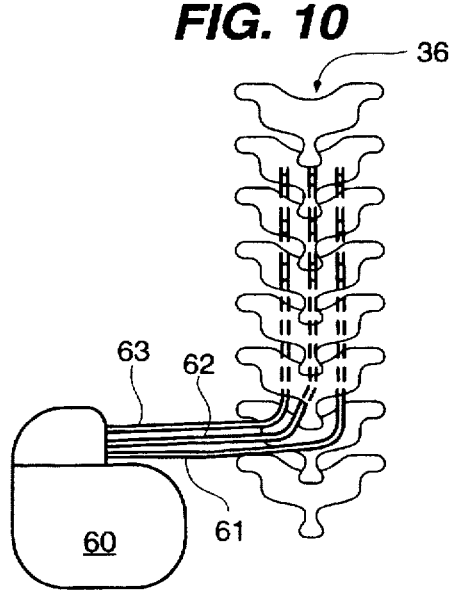
FIG. 10 is a block diagram of a three lead neural stimulator system constructed and operated according to the teachings of the present invention for steering an electric field.

FIG. 10 illustrates the use of a tri-channel stimulator 60 with anodic current control connected to three percutaneous-epidural leads 61–63. One lead 62 is placed within the epidural space at the midline proximal to the target vertebrate bodies 36, and the other two leads 61, 63 are placed at either side of the midline. Each electrode 71–79 in the leads 61–63 can be programmed positive (anode) or negative (cathode), and the anodic current at each positive electrode can be programmed to a value different from the other electrode, which electrode(s) serve as the cathode. The size and location of the stimulating field can be modulated for the purpose of recruiting only the target nerve tissue and exclude unwanted nerve tissue.

Figure 11:
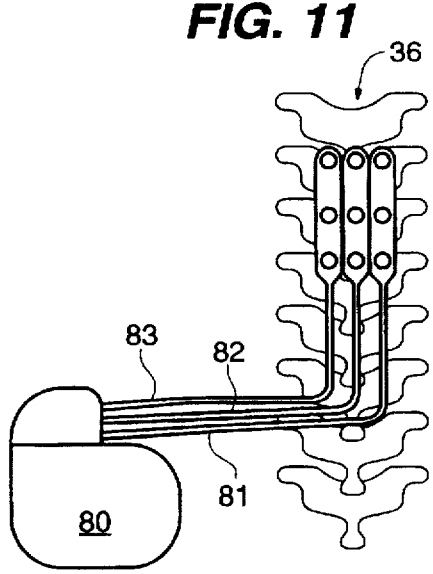
FIG. 11 is a block diagram of another three lead neural stimulator system constructed and operated according to the teachings of the present invention for steering an electric field.

FIG. 11 illustrates the use of a tri-channel stimulator 80 with anodic current control connected to three laminectomy leads 81–83. One lead 82 is placed at the midline proximal to the target vertebrate bodies, and the other two leads 81, 83 are placed at either side of the midline. Each electrode 71–79 in each lead 81–83 can be programmed positive (anode) or negative (cathode), and the anodic current at each positive electrode can be programmed to a value different from other anodes. Depending on the anodic current assigned to each electrode and which electrode(s) serve as the cathode, the size and location of the stimulating field can be modulated for the purpose of recruiting only the target nerve tissue and exclude unwanted nerve tissue.

Figure 12:
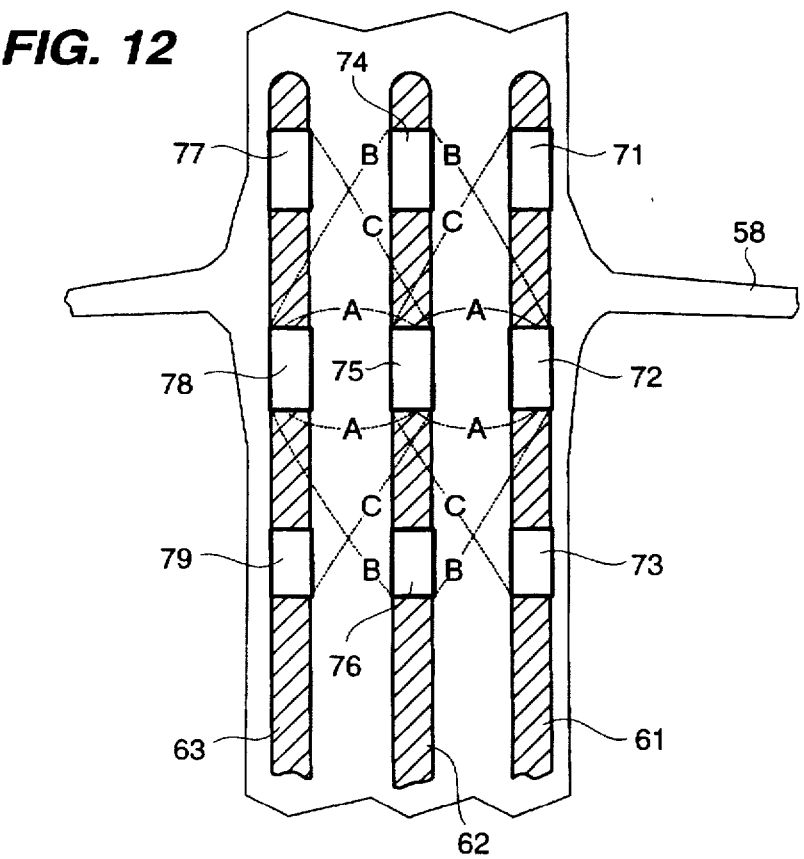
FIG. 12 is a longitudinal sectional view through the three distal tips of the three leads shown in FIG. 5 and shows three electric field configurations established therewith.

FIG. 12 illustrates how the size and location of the electric field can be modified by the neural stimulating system of the present invention to achieve a paresthesia pattern covering the pain area without recruiting unwanted nerve tissue. One lead 62 is placed at the midline proximal to the target vertebrate bodies, and the other two leads 61, 63 are placed at either side of the midline. Each electrode 71–79 in each lead 61–63 can be programmed positive (anode) or negative (cathode), and the anodic current of each positive electrode can be programmed to a value different from the other anodes. Depending on the anodic current assigned to each electrode and which electrode(s) serve as the cathode, the size and location of the stimulating field, A, B or C, can be modulated for the purpose of recruiting only the target nerve tissue and exclude unwanted nerve tissue. In this example, only three electric fields are shown but it is obvious that many more are possible.

Electric field A is obtained by programming electrode 75 as the cathode, and the electrodes 72 and 78 as anodes. The resulting electric field is contained within the two anodes (away from nerve root 58), with the size of the electric fields at the left and right sides determined by the anodic current programmed at the electrodes 72 and 78.

Electric field B is obtained by programming the electrodes 74, 75 and 76 as cathodes and the electrodes 72 and 78 as anodes. The resulting electric field is contained within the two anodes (away from nerve root 58). The size of the electric fields at the left and right sides is determined by the anodic current programmed at the electrodes 72 and 78.

Electric field C is obtained by programming electrode 75 as the cathode, and the electrodes 73, 72, 71, 77, 78 and 79 as anodes. The resulting electric field is contained within the anodes (away from nerve root 58). The size of the electric fields at the left and right sides is determined by the anodic current programmed at the electrodes 73, 72, 71, 77, 78 and 79.

Figure 13:
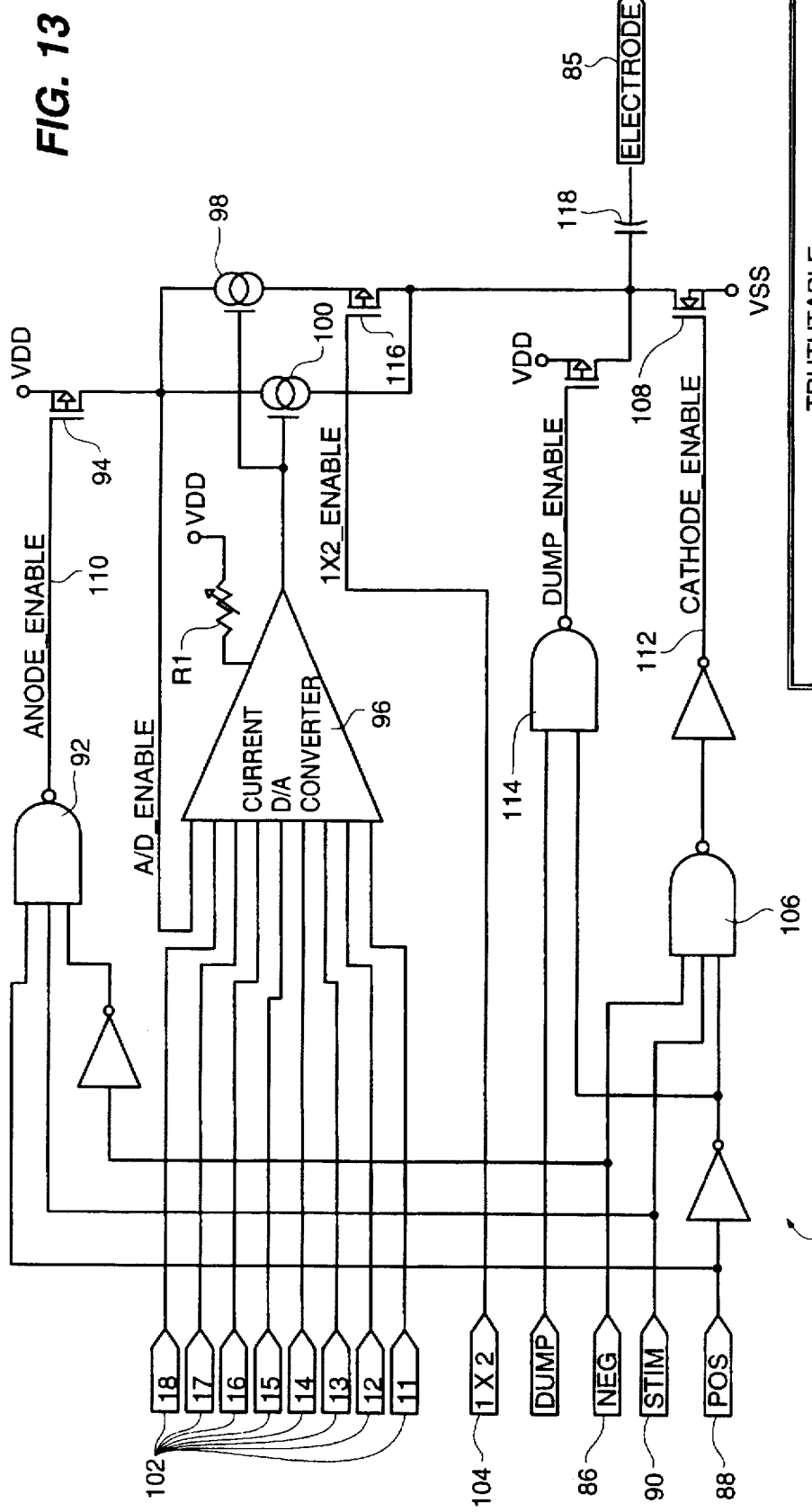
FIG. 13 is a block electrical schematic circuit diagram of the electrical circuit used to program each electrode as a constant current anode (+), a constant voltage cathode (−), or an open circuit, with a truth table of the inputs to the electrical circuit set forth in TABLE C.

FIG. 13 illustrates one electrical circuit 80 used in the present invention to program each electrode as a constant current anode (+), a constant voltage cathode (−), or open circuit. When an electrode 85 is programmed as an anode, it sources a constant current equal to a programmed value in milliamperes. When the electrode 85 is programmed as a cathode, it sources a constant negative voltage during each stimulus pulse. When the electrode 85 is programmed off, it becomes a high impedance, exceeding 1,000,000 Ohms (practically an open circuit). The logic state of inputs 86 and 88 determine if the electrode 85 is to be a cathode (−), an anode (+) or open circuit.

To program the electrode 85 as a constant current anode, input 86 is set to a logic 0 and input 88 is set to a logic 1. For the duration of each positive pulse applied to an input 90, a NAND 92 will switch on a transistor 94 which will enable a D/A converter 96 to regulate current sources 98/100 to deliver the milliampere value represented by inputs 102 and 104. Because input 88 is a logic 1, a NAND 106 is disabled keeping a transistor 108 off.

To program the electrode 85 as a cathode (−), input 86 is set to a logic one and input 88 is set to logic zero, disabling NAND 92 which makes a NAND output line 110 a logic 0 and turns off transistor 94 (the path from the electrode 85 to Vdd is blocked). However, the NAND 106 is enabled making a NAND output line 112 a logic 1 for the duration that input 90 is a logic 1, turning on transistor 108 which connects electrode 85 to Vss. After the stimulus pulse, line 86 switches to a logic 1 for a period controlled by a microcontroller or external logic, enabling a NAND 114 to turn on a transistor 116, discharge a coupling capacitor 118 and depolarizing the electrode 85.

To program the electrode 85 to open circuit, both inputs 86 and 88 must be set to the same logic level (either one or zero) to disable both NANDS 106 and 92 so that both transistors 94 and 108 are turned off at all times, disconnecting any path between the electrode 85 and Vdd or Vss.

Figure 14:
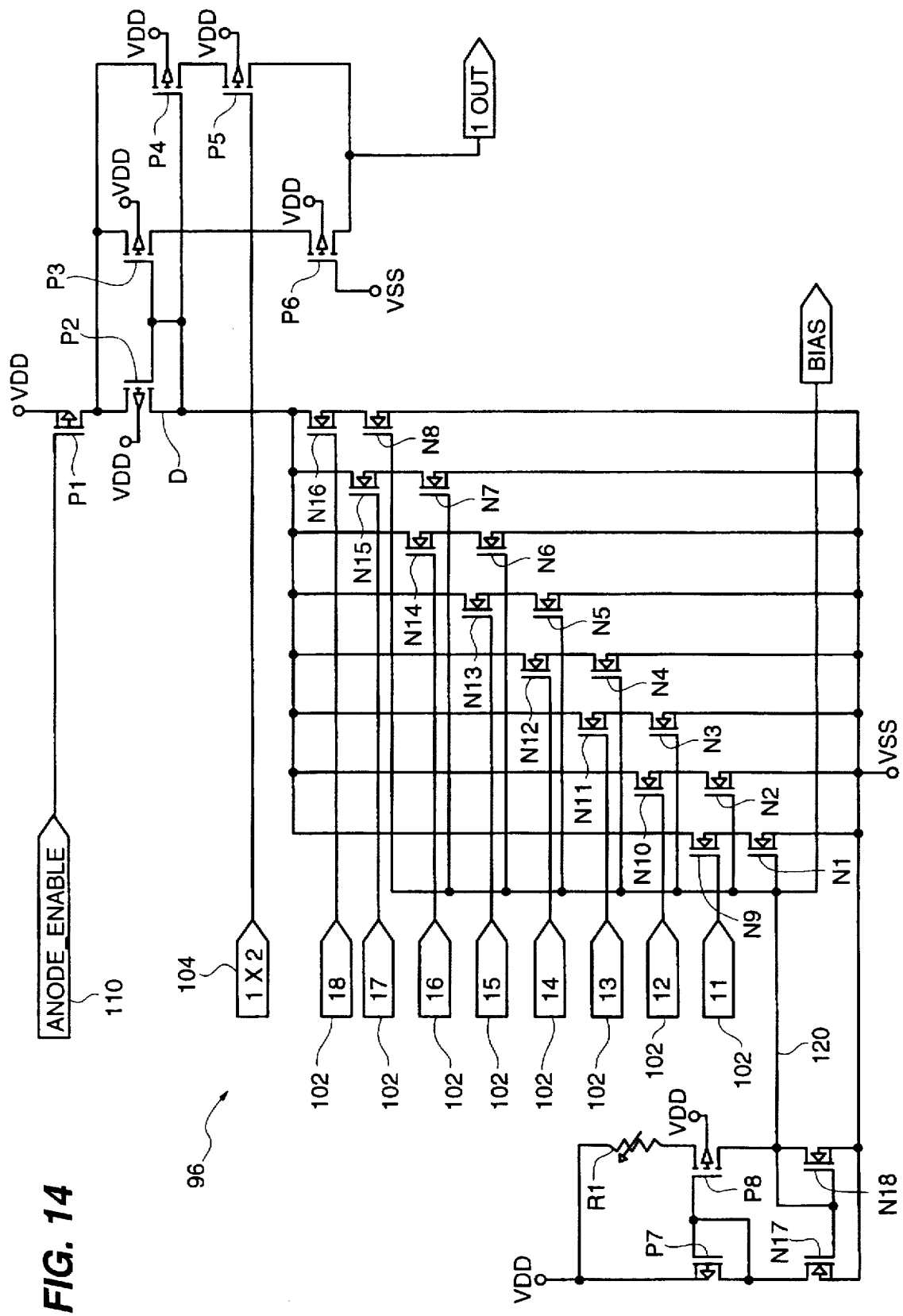
FIG. 14 is a block electrical schematic circuit diagram of a D/A converter of the electrical circuit shown in FIG. 13.

FIG. 14 illustrates the electrical circuit configuration of the D/A converter 96 used to regulate the anodic current. This circuit is better suited for implantation in a custom integrated circuit where all transistors can be closely matched. Transistors N16, N17, P7 and P8 form a feedback loop which tends to oppose any change in the current flowing through the resistor R1 (current trim resistor) as the supply voltage changes, thus maintaining a constant current.

Line 120 provides the bias voltage to the gates of transistors N1, N2, N3, N4, N5, N6, N7 and N8 which mirror a multiple of the current flowing through transistor N18 by virtue of having binary weighted channel width/length. For example, transistor N1 is an X1 mirror while transistor N8 is a X128 mirror, therefore the current flowing through transistor N1 equals the current flowing through transistor N18, but the current flowing through transistor N8 is 128 times that of the current flowing through the transistor N18.

Line 122 is a "current summation point" where all the currents are joined at the drain D of the transistor P2. Inputs 102 control which of the current multiples will pass up to the line 122 by switching on a combination of transistors N9, N10, N11, N12, N13, N14, N15 or N16 equivalent to the binary value applied to the inputs 102. This will allow current to flow through the transistors P1, P2 and into the selected combination of transistors N1 through N8, setting up a current mirror between transistors P2, P3 and P4. If input line 104 is a logic one this will switch off transistor P5, resulting in an anodic current at the electrode 85 equal to 20 times the current at transistor P2. However, if input line 104 is a logic zero, this will switch on transistor P5 and the anodic current will be doubled to 40 times the current at transistor P2. Therefore, the electrical circuitry of the present invention is capable of programming the anodic constant current at the electrode 85 in 512 equal steps.

Figure 15:
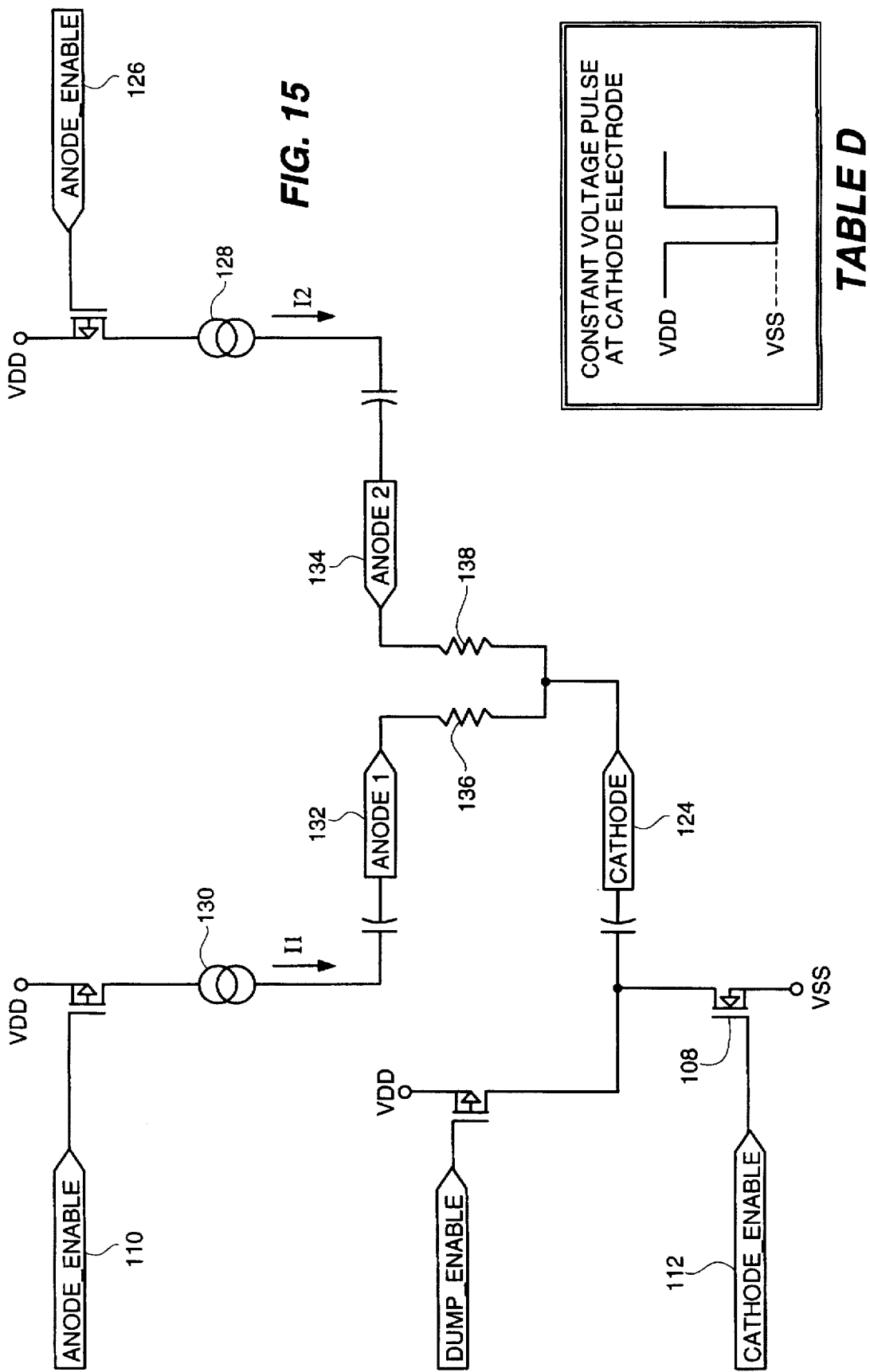
FIG. 15 is a block electrical schematic circuit diagram of circuitry for the current paths between one constant voltage cathode and two independent constant current anodes with a constant voltage pulse supplied at the cathode electrode illustrated in TABLE D.

FIG. 15 illustrates the stimulation current paths between one constant voltage cathode and two independent constant current anodes. During the stimulus pulse, input line 112 switches to a logic 1 turning on the transistor 108 which connects a cathode 124 to the negative supply VSS. Simultaneously, inputs 110 and 126 will switch to a logic 0 allowing independent current sources 128 and 130 to source anodic currents I1 and I2 to anodes 132 and 134, respectively. As previously stated, according to the teachings of the present invention, each anode can be programmed to a different current value, allowing the electric field to be stronger at the higher current anode than at the lower one, thus providing means for: 1) electronically steering the electric field towards the target nerve, 2) maintaining the electric field focused at the target nerve even when changes in electrode impedances 136 and 138 occur, by automatically changing the positive voltage at anodes 132 and 134 as required in order to maintain currents Ii and I2 constant, thereby preserving for the duration of the therapy, the original electric field found to be effective at implant time. A constant voltage pulse at the cathode electrode 124 is shown in TABLE D.

FIG. 16 illustrates a stimulating lead 140 having a tip 142 which can be deflected and rotated.

FIG. 17 is a block diagram of a lead steering assembly 144 and associated components of the electric field steering assembly of the present invention. As shown, the electric field steering assembly includes an external pulse generator 145 or an implantable pulse generator 146, a coupling lead 147 and the lead steering assembly 144. The lead steering assembly 144 includes a steering mechanism 148 which is used to maneuver a mandrel or stylet 149 mounting at its distal end 150, the distal end 142 of the stimulating lead 140 (FIG. 17) around anatomical obstacles within the epidural space and into a position adjacent to the dura for the purpose of recruiting only the target nerve tissue and exclude unwanted nerve tissue.

The construction of the stimulating lead 140 is shown in FIG. 18.

The construction of the flexible tip 150 of the steering assembly 144 is shown in cross section in FIG. 19.

The function of the lead 140 and the lead tip 142 shown in FIG. 19 is to carry the electrical stimuli from the pulse generator 145 or 146 to the target tissue. Such leads 140 are usually constructed of extruded tubular insulator material containing one or more electrodes 151–154 (FIG. 19). In order to improve pushability during placement, the lead contains a lumen (inside diameter) where the stylet 149 (FIG. 17) is introduced during placement. Introduction of the stylet 149 provides additional rigidity to the lead 140 during placement of the lead 140.

In this respect, the lumen inside the lead 140 is utilized to introduce the stylet 149 into a lead body 160 which has a proximal end 161 adapted to be connected to the self contained steering mechanism 148. The lead body 160 has a deflecting soft tip 142 as shown in FIG. 18.

The steering mechanism 148 includes a steering assembly handle 162 and a slide 164 mounted on the steering assembly handle 162 which is used to pull or push a wire 158 to deflect or steer the distal tip 150 mounting the lead's soft tip 142 to facilitate maneuvering and advancing the lead 140 within the spinal column epidural space. The slide 164 and handle 162 have cooperating detents and dimples or other locking mechanism for releasably locking the slide 164 in one of several longitudinal positions on the handle 162.

In order to allow electrical stimulation simultaneous with lead manipulation and placement, the steering assembly handle 162 is equipped with electrical contacts 171–174 which allow proximal electrodes 181–184 on the proximal end 161 of the lead body 160 (FIG. 19) to be mechanically and electrically connected to the contacts 171–174 and to extend that connection to an adapter 186 (FIG. 17) which in turn can be connected to the pulse generator 145 or 146.

The steering assembly 144 is a self contained reusable or disposable steering system aimed at facilitating the introduction, advancement and placement procedure for spinal leads. The system works best when used in a lead containing a soft distal tip 142 so as to allow effective tip deflection and achieve a higher level of maneuverability within the epidural space. Once lead placement is achieved, the physician can either remove the steering assembly 144 from the lead or crimp-cut the wire 158 and the proximal end of a NITINOL microtube 188 (FIG. 17) of a NITINOL microtube stylet assembly 149 including the wire 158 and the microtube 188 if a permanent deflection to anchor the leads electrode system is desired. If the latter approach is selected, the deflected lead can be removed from the handle 162 by retracting contacts 171–174 after crimping-cutting the steerable NITINOL microtube stylet assembly 149.

A distal deflection of a flat tip 192 received within a coiled, easily bendable, soft wire segment 194 at the distal end 150 of the stylet 149 facilitates deflection in one direction and a 360° deflecting orientation can be achieved by rotating the steering system handle 162.

The flexible tip 150 of the steering assembly 144 can be made without the coil wire 194 shown in FIG. 17 and instead a distal end portion 200 of the NITINOL tubing 188 can be ground down to provide a flexible distal end portion 200.

Then, a cone shaped tip member 202 is eccentrically attached to an end 204 of the pull wire 158, as shown.

With this construction of the distal end portion or tip 200 of the steering assembly 144, the NITINOL tubing 188 is caused to bend in the reduced-in-diameter end portion 200 when the pull wire 158 is pulled toward the handle 162.

Figure 20:
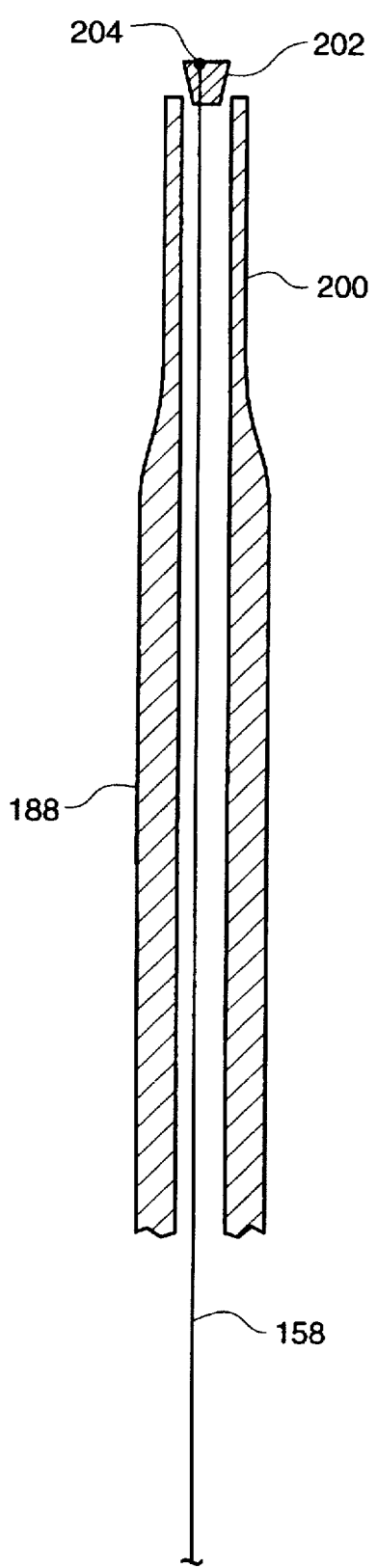
FIG. 20 is an enlarged longitudinal sectional view of another tip for the steering mechanism shown in FIG. 17.
Figure 21:
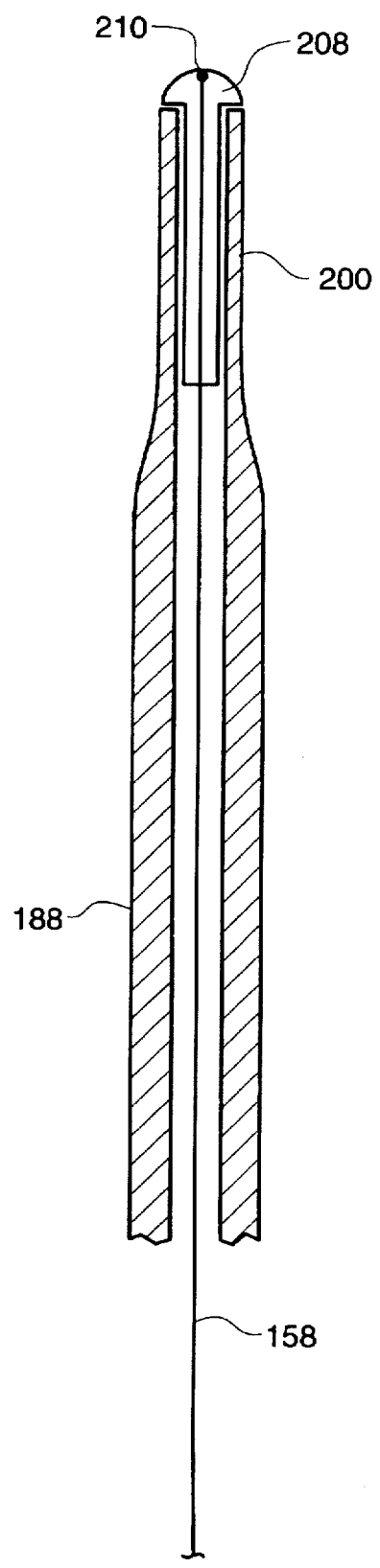
FIG. 21 is an enlarged longitudinal sectional view of still another tip for the steering mechanism shown in FIG. 17.

In FIG. 21 there is illustrated still another way of constructing the flexible tip of 150 of the steering assembly. Here the construction of the NITINOL tubing 188 in the distal end portion 200 thereof is substantially the same as that shown in FIG. 20. However, instead of having a cone shaped tip member 202, the embodiment shown in FIG. 20 has a flat tip member 208, similar to the tip member 192 shown in FIG. 19 and a distal end 210 of the wire 158 is fixed to a distal end of the flat tip member 208. Again, pulling of the pull wire 158 will cause the flat tip member 208 to move to one side so as to cause the reduced-in-diameter end portion 200 of the NITINOL tube 188 to bend.

From the foregoing description, it will be apparent that the electric field steering assembly of the present invention has a number of advantages, some of which have been described above and others of which are inherent in the invention. Also it will be understood that modifications can be made to the electric field steering assembly and components thereof described above without departing from the teachings of the present invention. Accordingly, the scope of the invention is only to be limited as necessitated by the accompanying claims.

We claim:

1. An implantable electric field steering assembly for controlling the size and/or location of, and/or steering the position of, an electric field in a living creature, said assembly comprising a pulse generator, at least one implantable lead coupled to said pulse generator and having, at a distal end thereof, at least first and second spaced apart anode electrodes and one cathode electrode, and electrical circuitry for programming at least two independent anodic (+) constant currents and at least one cathodic (−) constant voltage, said anodic (+) constant currents being coupled to said first and second anode electrodes in said lead and said cathodic voltage being coupled to said third cathode electrode in said lead and said electrical circuitry being programmed to electronically change the size and/or location of an electric field established between said electrodes by independently adjusting the current flowing from said first and second anode electrodes into said third cathode electrode, thereby steering the size and location of the electric field to recruit only certain target tissue and exclude unwanted tissue.

2. The electric field steering assembly of claim 1 including means for electronically steering an electric field towards a target nerve and for maintaining the electric field focused at the target nerve located between said third cathode electrode and said first and second anode electrodes and means for maintaining said electric field focused at the target nerve even when changes of impedance occur between said third cathode electrode and said first and second anode electrodes by automatically changing the positive voltage at said first and second anode electrodes.

3. An electric field steering assembly for controlling the size and/or location of, and/or steering the position of, an electric field in a living creature, said assembly comprising a pulse generator, at least one implantable lead coupled to said pulse generator and having, at a distal end thereof, at least two spaced apart anode electrodes and one cathode electrode, and electrical circuitry in said pulse generator and coupled to said electrodes for adjusting at least two anodic currents and at least one cathodic voltage at said respective electrodes, said electrical circuitry being programmed to electronically change the size and/or location of an electric field established between said electrodes by independently programming the current flowing through said anode (+) electrode(s) from said cathode (−) electrode, thereby steering the size and location of the electric field to recruit only certain tissue and exclude unwanted tissue said electrical circuitry being programmed to automatically change the voltage amplitude at each anode in response to changes in electrode impedance in order to maintain a constant anodic current, thereby preserving, for the duration of the therapy, the original electric field found to be effective at implant time.

4. The electric field steering assembly of claim 2 wherein said pulse generator is an implantable stimulator.

5. An electric field steering assembly for controlling the size and/or location of, and/or steering the position of, an electric field in a living creature, said assembly comprising a pulse generator, a first implantable lead coupled to said pulse generator and having, at a distal end thereof, at least two spaced apart anode electrodes and one cathode electrode, and electrical circuitry in said pulse generator and coupled to said electrodes for adjusting at least two anodic currents and at least one cathodic voltage at said respective electrodes, said electrical circuitry being programmed to electronically change the size and/or location of an electric field established between said electrodes by independently programming the current flowing through said anode (+) electrode(s) from said cathode (−) electrode, thereby steering the size and location of the electric field to recruit only certain tissue and exclude unwanted tissue and a second implantable lead having, at its distal end, at least three electrodes, and being coupled to said pulse generator.

6. The electric field steering assembly of claim 5 including a third lead having, at its distal end, at least three electrodes, and being coupled to said pulse generator.

7. An electric field steering assembly for controlling the size and/or location of, and/or steering the position of, an electric field in a living creature, said assembly comprising a pulse generator, at least one implantable lead coupled to said pulse generator and having, at a distal end thereof, at least two spaced apart anode electrodes and one cathode electrode, electrical circuitry in said pulse generator and coupled to said electrodes for adjusting at least two anodic currents and at least one cathodic voltage at said respective electrodes, said electrical circuitry being programmed to electronically change the size and/or location of an electric field established between said electrodes by independently programming the current flowing through said anode (+) electrode(s) from said cathode (−) electrode, thereby steering the size and location of the electric field to recruit only certain tissue and exclude unwanted tissue and a self contained steering mechanism independent of said lead which has a lumen therein, said steering mechanism being introduced through said lumen of said lead for steering or deflecting said distal tip of said lead for guidance and placement of said electrodes on said distal tip of said lead.

8. The self contained steering mechanism of claim 7 including a proximal lead connector coupled to said at least one implantable lead and an adapter for coupling said connector to said pulse generator.

9. The self contained steering mechanism of claim 7 including a proximal handle and a slide/brake assembly mounted on said handle for effecting deflection of said distal tip and/or for holding said deflected distal tip in one position.

10. The self contained steering mechanism of claim 9 including means for releasably locking said slide/brake assembly in a desired position for facilitating steering of said deflected distal tip of said lead.

11. The self contained steering mechanism of claim 7 including a deflectable tip, an highly elastic nickel-titanium tube and an internal pull wire mounted in said tube for facilitating deflection of said deflectable tip.

12. The electric field steering assembly of claim 7 wherein said at least one implantable lead comprises a tubular body having said lumen, a distal end portion including a flexible distal tip, at least three spaced apart electrodes on said distal end portion, a proximal end having at least three spaced apart electrodes thereon each electrically connected to one of said distal electrodes and an open proximal end for permitting said self contained steering mechanism to be inserted into said open end and through said lumen to said deflectable tip.

13. An electric field steering assembly of for controlling the size and/or location of, and/or steering the position of, an electric field in a living creature, said assembly comprising a pulse generator, at least one implantable lead coupled to said pulse generator and having, at a distal end thereof, at least two spaced apart anode electrodes and one cathode electrode, and electrical circuitry in said pulse generator and coupled to said electrodes for adjusting at least two anodic currents and at least one cathodic voltage at said respective electrodes, said electrical circuitry being programmed to electronically change the size and/or location of an electric field established between said electrodes by independently programming the current flowing through said anode (+) electrode(s) from said cathode (−) electrode, thereby steering the size and location of the electric field to recruit only certain tissue and exclude unwanted tissue, said electrodes including a left anode electrode, a center cathode electrode and a right anode electrode and said electric field being steered by establishing a zero voltage on said cathode electrode and forcing a first constant current at one of the other anode electrodes and another constant current at the remaining anode electrode.

14. An electric field steering assembly for controlling the size and/or location of, and/or steering the position of, an electric field in a living creature, said assembly comprising a pulse generator, at least one implantable lead coupled to said pulse generator and having, at a distal end thereof, at least two spaced apart anode electrodes and one cathode electrode, and electrical circuitry in said pulse generator and coupled to said electrodes for adjusting at least two anodic currents and at least one cathodic voltage at said respective electrodes, said electrical circuitry being programmed to electronically change the size and/or location of an electric field established between said electrodes by independently programming the current flowing through said anode (+) electrode(s) from said cathode (−) electrode, thereby steering the size and location of the electric field to recruit only certain tissue and exclude unwanted tissue, said electrical circuitry including means for programming each electrode comprising a cathode enable circuit having an output, an anode enable circuit having an output, current generating means having an output and a D/A converter circuit having an output coupled to said current generating means, said output of said anode enable circuit also being coupled to said current generating means and said output of said current generating means and said output of said cathode enable circuit being coupled to one of said anode electrodes.

15. An electric field steering assembly for controlling the size and/or location of, and/or steering the position of, an electric field in a living creature, said assembly comprising a pulse generator, at least one implantable lead coupled to said pulse generator and having, at a distal end thereof, at least two spaced apart anode electrodes and one cathode electrode, and electrical circuitry in said pulse generator and coupled to said electrodes for adjusting at least two anodic currents and at least one cathodic voltage at said respective electrodes, said electrical circuitry being programmed to electronically change the size and/or location of an electric field established between said electrodes by independently programming the current flowing through said anode (+) electrode(s) from said cathode (−) electrode, thereby steering the size and location of the electric field to recruit only certain tissue and exclude unwanted tissue, said electrical circuitry including: a cathode enable circuit coupled to said cathode electrode; a first current enable circuit coupled to a first current generator which, in turn, is coupled to a first anode defined by one of said anode electrodes; a second anode enable circuit coupled to a second current generator which, in turn, is coupled to a second anode defined by the remaining anode electrode.

16. A method for steering and/or controlling the size and position of an electric field in a living creature including the steps of:

providing a pulse generator;

implanting the pulse generator in living tissue providing at least one implantable lead having at least a first anodic electrode, a second anodic electrode and a third cathodic electrode at a distal end thereof;

implanting the distal end adjacent a target tissue in the living creature;

establishing an electric field between said electrodes; and, electronically changing the size and/or location of said electric field by independently programming the current flowing through said first and second anodic electrodes from said third cathodic electrode thereby steering the size and location of said electric field to recruit only selected tissue and exclude unwanted tissue.

13

17. The method of claim 16 wherein said step of implanting said lead includes the steps of steering said distal end of said at least one lead to a desired position adjacent a target nerve.

18. The method of claim 17 wherein said step of steering said distal end of said lead includes the steps of bending said distal end of said lead and the step of rotating said lead.

19. A method for steering and/or controlling the size and position of an electric field in a living creature including the steps of:
providing a pulse generator;
implanting the pulse generator in living tissue
providing at least one implantable lead having at least a first anodic electrode, a second anodic electrode and a third cathodic electrode at a distal end thereof;
implanting the distal end adjacent a target tissue in the living creature by steering said distal end of said at least one lead to a desired position adjacent a target nerve by bending said distal end of said lead and rotating said lead and releasably locking said bent distal end of said lead in a selected position adjacent the target tissue;
establishing an electric field between said electrodes; and,
electronically changing the size and/or location of said electric field by independently programming the current flowing through said first and second anodic electrodes from said third cathodic electrode thereby steering the size and location of said electric field to recruit only selected tissue and exclude unwanted tissue.

20. A method for steering and/or controlling the size and position of an electric field in a living creature including the steps of:
providing a pulse generator;
implanting the pulse generator in living tissue
providing at least one implantable lead having at least a first anodic electrode, a second anodic electrode and a third cathodic electrode at a distal end thereof;
implanting the distal end adjacent a target tissue in the living creature;
establishing an electric field between said electrodes; and,
electronically changing the size and/or location of said electric field by independently programming the current flowing through said first and second anodic electrodes from said third cathodic electrode thereby steering the size and location of said electric field to recruit only selected tissue and exclude unwanted tissue, said electric field being established by establishing a zero voltage on said cathodic electrode; forcing a first constant current at one of said anodic electrodes; and forcing a second constant current at the remaining anodic electrode; and said step of steering said electric field is accomplished by changing the voltage and/or currents at the three electrodes.

21. A method for steering and/or controlling the size and position of an electric field in a living creature including the steps of:
providing a pulse generator;
implanting the pulse generator in living tissue
providing at least one implantable lead having at least a first anodic electrode, a second anodic electrode and a third cathodic electrode at a distal end thereof;

14 implanting the distal end adjacent a target tissue in the living creature;
establishing an electric field between said electrodes; electronically changing the size and/or location of said electric field by independently programming the current flowing through said first and second anodic electrodes from said third cathodic electrode thereby steering the size and location of said electric field to recruit only selected tissue and exclude unwanted tissue; and, maintaining said electric field focused at a target nerve located near said cathodic electrode and said first and second anodic electrodes when changes in impedance occur between said cathodic electrode and said first and second anodic electrodes by automatically changing the positive voltage at said first and second anodic electrodes.

22. A method for steering and/or controlling the size and position of an electric field in a living creature including the steps of:
providing a pulse generator;
implanting the pulse generator in living tissue
providing at least one implantable lead having at least a first anodic electrode, a second anodic electrode and a third cathodic electrode at a distal end thereof;
implanting the distal end adjacent a target tissue in the living creature;
establishing an electric field between said electrodes; electronically changing the size and/or location of said electric field by independently programming the current flowing through said first and second anodic electrodes from said third cathodic electrode thereby steering the size and location of said electric field to recruit only selected tissue and exclude unwanted tissue; and, automatically changing the voltage amplitude at each anodic electrode in response to changes in electrode impedance in order to maintain a constant anodic current, thereby preserving for the duration of the therapy the electric field found to be effective at implant time.

23. For use in an electric field steering assembly, a self contained steering mechanism independent from a stimulating lead, said steering mechanism being introduced through a lumen of the lead for steering or deflecting a distal tip of the lead for guiding and placement of electrodes on the distal tip of the lead, said steering mechanism including a deflectable tip, a highly elastic nickel-titanium alloy tube and an internal pull wire mounted in said tube for facilitating deflection of said deflectable tip and said deflectable tip being defined by a reduced-in-diameter distal end portion of said nickel-titanium alloy tube.

24. The self contained steering mechanism of claim 23 further including a cone shaped tip member and said pull wire having a distal end which is eccentrically connected to said cone shaped tip member.

25. The self contained steering mechanism of claim 23 further including a flat tip member mounted in the outer end of said nickel-titanium alloy tube and said pull wire being connected to said flat tip member near a distal end thereof.

* * * * *